US012416577B2

(12) United States Patent
Raveendran et al.

(10) Patent No.: US 12,416,577 B2
(45) Date of Patent: Sep. 16, 2025

(54) SENSOR ELEMENTS HAVING METALLIC NANOSTRUCTURES AND USES THEREOF

(71) Applicant: Queen's University at Kingston, Kingston (CA)

(72) Inventors: Joshua Raveendran, Timmins (CA); Hannah Bacon, Toronto (CA); Carlos Escobedo, Kingston (CA); Aristides Docoslis, Kingston (CA)

(73) Assignee: Queen's University at Kingston, Kingston (CA)

( * ) Notice: Subject to any disclaimer, the term of this patent is extended or adjusted under 35 U.S.C. 154(b) by 38 days.

(21) Appl. No.: 17/607,611

(22) PCT Filed: Apr. 29, 2020

(86) PCT No.: PCT/CA2020/050571
§ 371 (c)(1),
(2) Date: Oct. 29, 2021

(87) PCT Pub. No.: WO2020/220131
PCT Pub. Date: Nov. 5, 2020

(65) Prior Publication Data
US 2022/0221407 A1 Jul. 14, 2022

Related U.S. Application Data

(60) Provisional application No. 62/842,188, filed on May 2, 2019.

(51) Int. Cl.
*G01N 21/65* (2006.01)
*A61B 5/1468* (2006.01)
*B82Y 15/00* (2011.01)

(52) U.S. Cl.
CPC ......... *G01N 21/658* (2013.01); *A61B 5/1468* (2013.01); *A61B 2562/028* (2013.01);
(Continued)

(58) Field of Classification Search
CPC .................. G01N 21/658; G01N 21/554
See application file for complete search history.

(56) References Cited

U.S. PATENT DOCUMENTS 6,558,956 B1    5/2003  Carron et al.
6,770,488 B1*   8/2004  Carron ............ G01N 33/54313
                                                            436/805
(Continued)

FOREIGN PATENT DOCUMENTS

CA      3033447 A1   2/2018
CN    104492509 B    8/2016
(Continued)

OTHER PUBLICATIONS

Wu, Xiaoling, et al. "Environmentally responsive plasmonic nanoassemblies for biosensing." Chemical Society Reviews 47.13 (2018): 4677-4696. (Year: 2018).*

(Continued)

Primary Examiner — Rufus L Phillips
(74) Attorney, Agent, or Firm — Stephen J. Scribner

(57) ABSTRACT

A sensor element comprises a metallic nanostructure formed at edges of at least two microelectrodes on a non-electrically conductive substrate. The nanostructure is formed by depositing a solution comprising at least one metal salt and a stabilizing agent on the substrate at a detection site between the microelectrodes, and applying an AC electric field to the electrodes. The sensor elements may be used in sensing platforms such as surface-enhanced Raman scattering (SERS), surface plasmon resonance (SPR), localized surface plasmon resonance (LSPR), and in electrical-based sensing such as electrochemical sensing.

24 Claims, 11 Drawing Sheets

(52) U.S. Cl.
CPC .. *A61B 2562/0285* (2013.01); *A61B 2562/125* (2013.01); *B82Y 15/00* (2013.01)

(56) References Cited

U.S. PATENT DOCUMENTS

| | | | |
|---|---|---|---|
| 7,449,757 | B2 | 11/2008 | Bradley et al. |
| 7,688,440 | B2 | 3/2010 | Clarke et al. |
| 8,792,095 | B2 | 7/2014 | Piorek |
| 9,255,842 | B2 | 2/2016 | Gardner et al. |
| 9,395,363 | B2 | 7/2016 | Valsesia et al. |
| 10,001,443 | B2 | 6/2018 | Gardner et al. |
| 11,237,112 | B2 | 2/2022 | Bacon et al. |
| 2010/0040979 | A1 | 2/2010 | Weimer |
| 2011/0165586 | A1 | 7/2011 | Kim et al. |
| 2012/0073358 | A1 | 3/2012 | Bhargava et al. |
| 2012/0134880 | A1 | 5/2012 | Kurkina et al. |
| 2012/0242987 | A1 | 9/2012 | Liu et al. |
| 2014/0083855 | A1 | 3/2014 | Cheng et al. |
| 2014/0125976 | A1 | 5/2014 | Kim et al. |
| 2015/0177138 | A1 | 6/2015 | Kim |
| 2015/0374268 | A1 | 12/2015 | Yarnakawa et al. |
| 2016/0202123 | A1* | 7/2016 | Jung .................. B29C 33/3857 156/232 |
| 2019/0331605 | A1* | 10/2019 | Park .......................... G01J 3/44 |
| 2020/0371035 | A1* | 11/2020 | Chen .................... G01N 21/658 |

FOREIGN PATENT DOCUMENTS

| | | | | |
|---|---|---|---|---|
| CN | 109187486 A | | 1/2019 | |
| CN | 109294234 A | * | 2/2019 | ............... C08J 5/18 |
| JP | 2014-517926 | | 7/2014 | |
| JP | 2015-26022 | | 2/2015 | |
| JP | 2016-099113 | | 5/2016 | |
| WO | WO2001025757 A1 | | 4/2001 | |
| WO | WO2010133849 A1 | | 11/2010 | |
| WO | WO2012/161683 A1 | | 11/2012 | |
| WO | WO2014188237 A1 | | 11/2014 | |
| WO | WO-2017046179 A1 | * | 3/2017 | ............. B82Y 20/00 |
| WO | WO2018/027309 A1 | | 2/2018 | |

OTHER PUBLICATIONS

Han, Xinyi, et al. "Ultrafast growth of dendritic gold nanostructures and their applications in methanol electro-oxidation and surface-enhanced Raman scattering." Journal of colloid and interface science 354.2 (2011): 577-584. (Year: 2011).*

Lin, Yang-Wei, and Chung Tang. "Electrochemical synthesis and deposition of surface-enhanced Raman scattering-active silver microstructures on a screen-printed carbon electrode." The Journal of Physical Chemistry C 119.44 (2015): 24865-24874. (Year: 2015).*

CN 105424676 A (Year: 2016).*

International Search Report and Written Opinion for corresponding International Application No. PCT/CA2020/050571 filed on Apr. 29, 2020.

International Search Report and Written Opinion for corresponding International Application No. PCT/CA2017/050931 filed on Aug. 4, 2017.

Wu, W., et al. "Low-Cost, Disposable, Flexible and Highly Reproducible Screen Printed SERS Substrates for the Detection of Various Chemicals", Scientific Reports 5:10208, pp. 1-9, 2015.

Carron, K., et al., "SERS: Instruments, Materials, and Applications for Defense and Security", Metrohm MP-SET-253-KNP, Metrohm AG.

Chowdhury, F. et al., "High Enhancement SERS Substrates Created Using DEP-DLA & Annealing Au-W", IEEE Sensors Proceeings, pp. 1-4, (2011).

Kim, M-S., et al., "Controlled Aggregation of Silver Nanoparticles Using DEP Force for SERS (Surface Enhanced Raman Spectroscopy) Analysis", IEEE Transducers the 13th International Conference on Solid-State Sensors, pp. 1768-1771, (2005).

Cheng, I-F., et al., "Rapid identification of bacteria utilizing amplified dielectrophoretic force-assisted nanoparticle-induced surface-enhanced Raman spectroscopy", Nanoscale Research Letters, vol. 9, pp. 1-8, (2014).

Dies, H. et al., "In situ assembly of active surface-enhanced Raman scattering substrates via electric field-guided growth of dendritic nanoparticle structures" Nanoscale, vol. 9, pp. 7847-7857, (2017).

Liu, C et al., "Electrokinetic Manipulation Integrated Plasmonic-Photonic Hybrid Raman Nanosensors with Dually Enhanced Sensitivity", ACS Sensors, vol. 2, pp. 346-353, (2017).

Extended European Search Report for corresponding European Application No. 17838252.9 dated Feb. 19, 2020.

Naja, G., et al., "Raman-based detection of bacteria using silver nanoparticles conjugated with antibodies", Analyst, vol. 132, pp. 679-686, (2007).

Chan, Y.F., et al., "Ag dendritic nanostructures as ultrastable substrates for surface-enhanced Ramen scattering", Applied Physics Letters, vol. 102, 183118, (2013).

Supplementary European Search Report for corresponding European application No. EP20798205.9 dated Nov. 24, 2022.

Nguyen, T-A. et al., "Effect of electrodeposition cycles on the performance of gold nanostructures as SERS-active substrates", Journal of Industrial and Engineering Chemistry, vol. 48, pp. 230-234, (2017).

Ji, J., et al., "Electrodeposition of Au/Ag bimetallic dendrites assisted by Faradaic AC-electroosmosis flow", AIP Advances, pp. 031329-1 to 031329-9, (2014).

* cited by examiner

SENSOR ELEMENTS HAVING METALLIC NANOSTRUCTURES AND USES THEREOF

FIELD

This invention relates to sensor elements having metallic nanostructures, to methods for forming metallic nanostructures using microelectrodes, and to uses of such sensor elements in sensing applications such as surface-enhanced Raman scattering (SERS), in surface plasmon resonance (SPR) or localized surface plasmon resonance (LSPR) platforms, and electrical-based chemical, biochemical, and biological sensing.

BACKGROUND

Fabrication of metallic structures with nanofeatures is an area of interest for plasmonic-based and electrochemical-based sensing applications. These applications rely heavily on the innate properties of the metals and how those properties interact with matter and light on the nanoscale. However, the properties of the metallic structure can vary greatly depending on its composition and features, which are largely determined by the fabrication process.

Fabrication using an electrolytic system to deposit metal ions results in the metallic structure being formed directly on a cathode with the use of a direct current (DC) electric field. The working electrode is a conductive surface dipped into a bath containing the metal ions. The counter electrode can be in the same bath or in a separate bath connected by a salt bridge. Surfactants, templates, or supporting electrolytes can all be included in the solution to influence deposition, or the process can be performed without additives. Additives provide more control over the electrodeposition process and open up new pathways for structure morphology but can also be incorporated into the structure, compromising the performance of the structure. Use of an alternating current (AC) field or a pulse-like electrical signal for electrochemical deposition is less common, and is carried out based on a setup similar to those used for DC fields.

There are only a few cases in which it was proposed to use microelectrodes to form dendritic nanostructures. In one case a well was placed on the electrodes and used to promote the growth of palladium dendrites (L. Soleymani, et. al, Nanostructuring of patterned microelectrodes to enhance the sensitivity of electrochemical nucleic acids detection, *Angew. Chemie*-Int. Ed., 48 (45): 8457-8460, 2009). At low potentials, the palladium formed smooth microelectrodes, and increasing the potential resulted in nanostructure electrodes. Subsequently it was found that microscale wells on an ITO glass were necessary to form dendrites using silver, gold, or platinum salts (S. Wang, et. al, Space-confined fabrication of silver nanodendrites and their enhanced SERS activity, *Nanoscale*, 5 (10): 4284-4290, 2013).

Without the wells, only nanoparticles formed on the surface of the ITO cathode. Using a 'large' well resulted in particles in the centre and dendrites on the side of the well. Decreasing the radius of the well resulted in only dendritic structures forming. Generally, the presence of an insulating well distorts the electric field with the electric field being strongest at the edges of the well, resulting in difficulty in controlling the nanostructure features.

Dendritic nanostructures were formed with microelectrodes using directed electrochemical nanowire assembly (DENA). DENA involves using a high frequency AC field in the kHz or MHz range. Metals were deposited as nanowires using DENA without a stabilizer or template to guide the assembly (J. Ji, et al., Electrodeposition of Au/Ag bimetallic dendrites assisted by Faradaic AC-electroosmosis flow, *AIP Adv.*, 4 (3), 2014; N. Ranjan, et al., Dielectrophoretic growth of metallic nanowires and microwires: Theory and experiments, *Langmuir*, 26 (1): 552-559, 2010; J. K. Kawasaki, et al., Synthesis of platinum dendrites and nanowires via directed electrochemical nanowire assembly, *Nano Lett.*, 11 (2): 781-785, 2011). The nanowires grow off of the tips of both electrodes where the electric field gradient is highest, toward one another, following the electric field lines. Increasing the frequency increases the growth rate of the wires but also makes them thinner, and lowering the frequency towards 1 kHz and below results in aggregate-like structures with no distinct structure, as well as deposition on the top of the electrodes. DENA is limited by the required high electric fields and electric field gradients which call for high applied voltages and small gaps between electrodes, typically 10 microns or less, which limits both the size and surface coverage of DENA based structures.

SUMMARY

According to one aspect of the invention there is provided a sensor element, comprising: a non-electrically conductive substrate; a metallic nanostructure disposed on the substrate; wherein the substrate has a surface property that promotes non-covalent adhesion of the metallic nanostructure; wherein the metallic nanostructure comprises at least one metal and at least one stabilizing agent.

According to various embodiments, the at least one metal may be derived from at least one metal salt. In one embodiment, the nanostructure is substantially 2-dimensional.

In various embodiments, the at least one metal salt comprises silver, gold, copper, platinum, aluminum, gallium, indium, rhodium, lithium, sodium, potassium, rubidium, or cesium, or a combination of one or more thereof.

In various embodiments, the at least one stabilizing agent comprises citrate, succinate, trans-aconate, SDS, PVP, or a combination of one or more thereof.

In one embodiment, the sensor element comprises at least two metal microelectrodes removably disposed on or in close proximity to the substrate in a spaced relationship such that a detection site is formed between opposing edges of the at least two microelectrodes.

In one embodiment, the metallic nanostructure is removably disposed on edges of the at least two microelectrodes.

Another aspect of the invention relates to a sensor platform comprising a sensor element as described herein.

In various embodiments, the sensor platform is selected from surface-enhanced Raman scattering (SERS), in surface plasmon resonance (SPR), localized surface plasmon resonance (LSPR), and electrical-based chemical, biochemical, and biological sensing.

In one embodiment, the sensor platform is a surface enhanced Raman spectroscopy device, comprising a sensor element as described herein.

According to another aspect of the invention there is provided a method for preparing a sensor element, comprising: disposing at least two metal microelectrodes in a spaced relationship on or in close proximity to a non-electrically conductive substrate such that a detection site is formed between opposing edges of the at least two microelectrodes; disposing a solution comprising at least one stabilizing agent and at least one metal salt on the substrate at the detection site; applying an AC electrical signal to the at least two microelectrodes; wherein the AC electrical signal creates an AC electric field that induces, directs, and/or influences the at least one metal salt to form a nanostructure at edges of the at least two microelectrodes; wherein a sensor element comprising a metallic nanostructure is prepared.

The method may comprise modifying a surface of the substrate to promote non-covalent adhesion of the metallic nanostructure to the surface.

The method may comprise modifying a surface of the substrate by exposing the surface to one or more agent that lowers a surface energy of the surface.

In various embodiments of the method, the at least one metal salt comprises silver, gold, copper, platinum, aluminum, gallium, indium, rhodium, lithium, sodium, potassium, rubidium, or cesium, or a combination of one or more thereof.

In various embodiments of the method, the at least one stabilizing agent comprises citrate, succinate, trans-aconate, SDS, PVP, or a combination of one or more thereof.

In one embodiment of the method, the at least one metal salt comprises silver nitrate and the at least one stabilizing agent comprises citrate.

In various embodiments, a ratio of concentration of citrate to concentration of silver nitrate is from 0.5:1 to 6:1.

In various embodiments, a concentration of citrate is from 0.5 mM to 10 mM.

In various embodiments, the AC electrical signal has a frequency in the range of 0.01 Hz to 100 Hz.

In one embodiment, the nanostructure is substantially 2-dimensional.

In one embodiment, the nanostructure is removably disposed at edges of the at least two microelectrodes. In one embodiment, the at least two microelectrodes are removed after the nanostructure is formed.

According to another aspect of the invention there is provided a method for analyzing a sample, comprising: applying the sample to the metallic nanostructure of a sensor element as described herein; and using a technique selected from surface-enhanced Raman scattering (SERS), surface plasmon resonance (SPR), and localized surface plasmon resonance (LSPR), or an electroanalytical technique selected from coulometry, amperometry, and voltammetry, to detect an analyte in the sample.

In one embodiment, an electric field is present at least during application of the sample.

According to embodiments, an analyte in the sample may be concentrated at the detection site.

In one embodiment, the sensor element comprises at least two metal microelectrodes disposed on or in close proximity to the substrate in a spaced relationship; wherein the metallic nanostructure is formed between opposing edges of the at least two microelectrodes; wherein the electric field is applied across the at least two electrodes.

BRIEF DESCRIPTION OF THE DRAWINGS

For a greater understanding of the invention, and to show more clearly how it may be carried into effect, embodiments will be described, by way of example, with reference to the accompanying drawings, wherein:

FIG. 1A, 0.9 Vpp; FIG. 1B, 1.00 Vpp; FIG. 1C, 1.25 Vpp; FIG. 1D, 1.50 Vpp; FIG. 1E, 1.75 Vpp; FIG. 1F, 2.00 Vpp; FIG. 1G, 2.25 Vpp; FIG. 1H, 2.50 Vpp; FIG. 1I, 3.00 Vpp; FIG. 1J, 3.50 Vpp; scale bar 100 microns.

FIGS. 2A, 2B) OL100 design; FIGS. 2C, 2D) MP40 design; FIGS. 2E, 2F) ID100 design; FIGS. 2G, 2H) DB100 design; scale bar is 100 microns.

DETAILED DESCRIPTION OF EMBODIMENTS

Figures 1A, 1B, 1C, 1D, 1E, 1F, 1G, 1H, 1I, 1J:
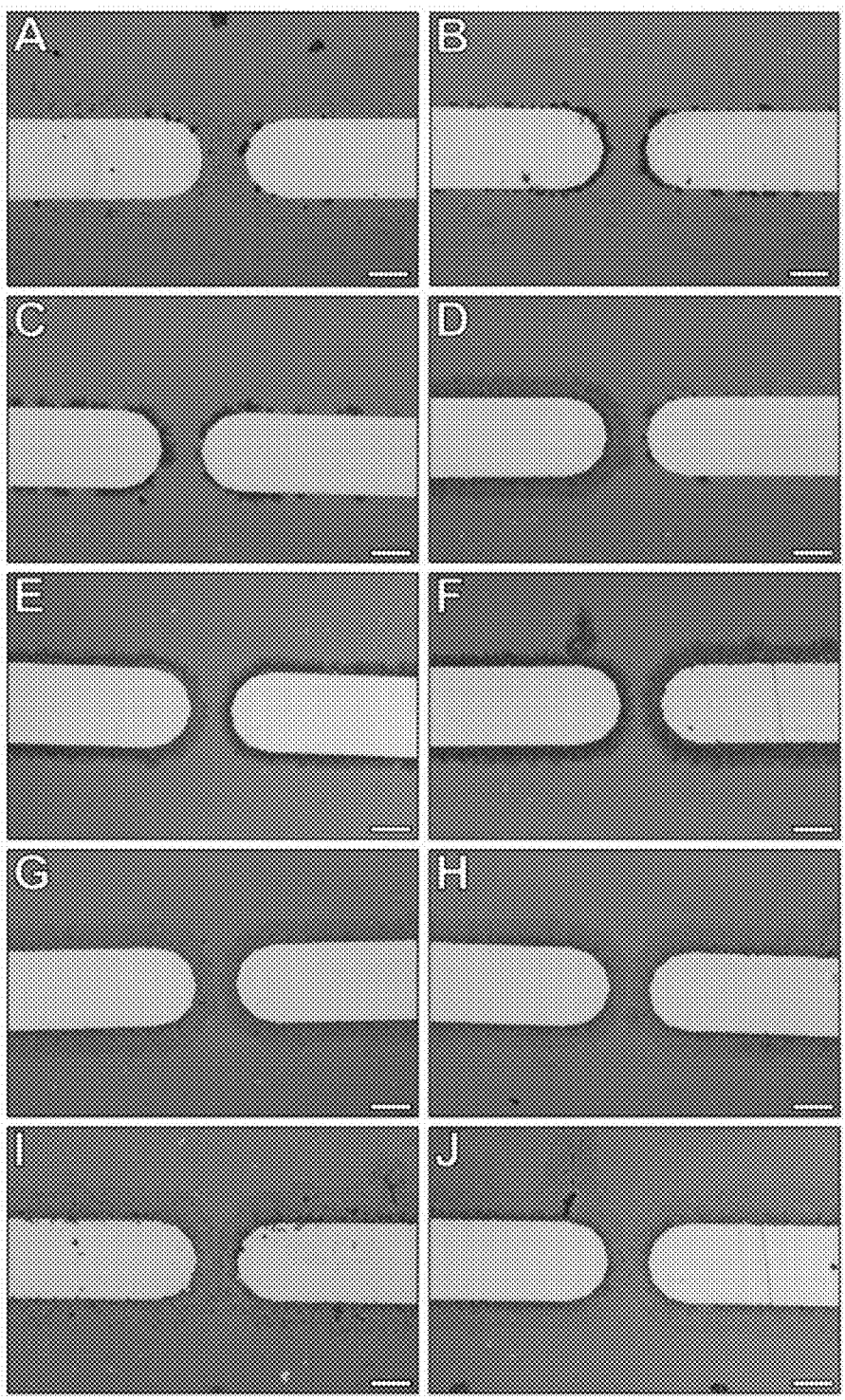
FIGS. 1A-1J are a series of photomicrographs showing effect of applied AC voltage (10 Hz sine wave) on nanostructure growth on electrodes with a 2/0.5 mM solution.

Described herein are sensor elements based on metallic nanostructures, and methods for preparing the sensor elements. In various embodiments the sensor elements include a non-electrically conductive substrate upon which the metallic nanostructure is disposed, and optionally one or more electrodes (also referred to herein as "microelectrodes") electrically connected to the metallic nanostructure. In various embodiments the methods may use a combination of one or more of an alternating current (AC) electric field, a stabilizing agent and metal salt solution, a microelectrode platform including metal electrodes, and a substrate with surface properties that promote and/or enhance formation of substantially 2-dimensional nanostructures, to reduce the metal salt and form the 2-dimensional nanostructures along edges of the metal electrodes. According to embodiments, the combination of electrical parameters, composition of the stabilizing agent and metal salt solution, together with proper electrode design and proper substrate surface properties ensure that only edges of the electrodes act as nucleation sites for nanostructure formation. Proper substrate surface properties are characterized by properties that remain relatively constant throughout nanostructure formation, and that promote interaction between the substrate and the growing nanostructure. In some embodiments, proper surface properties of the substrate are achieved by modifying the surface properties, e.g., through chemical treatment.

As used herein, the term "metallic nanostructure" refers to a nanostructure that is grown from a solution, wherein reactants in the solution are at least one metal salt and at least one stabilizing agent. In some embodiments, the solution may include other reactants or ingredients. Metallic nanostructure growth as described herein requires at least one metal salt and proceeds via reduction of metal ions. Metallic nanostructures may be branched, clustered, aggregated, fractal, and/or dendritic structures, formed from a single metal salt, or a mix of two or more metal salts. It will be appreciated that the metallic nanostructures and methods described herein are not based on nanoparticles, although it is possible that some nanoparticles may be present in the solution (e.g., through spontaneous nanoparticle formation or contamination). However, metallic nanostructures and methods described herein are distinct from structures that are based on assembly of nanoparticles, at least insofar as assembly of nanoparticles does not involve reduction of metal ions. Moreover, based on methods and embodiments described herein, it is expected that nanoparticles, if present in the solution, would not be uniformly incorporated into metallic nanostructures, possibly negatively affecting their stability and/or performance.

As the metal ions are reduced, the nanostructure grows outwards away from the electrode edge in a substantially 2-dimensional arrangement (i.e., in the same plane as the substrate), rather than 3-dimensions. Insofar as the nanostructure growth may be similar to a Volmer-Weber mode (Z. Xi, et al., Engineered noble-metal nanostructures for in vitro diagnostics, *Chem. Mater.*, 30 (23): 8391-8414, 2018), it is suggested herein that the metal ions undergo direct electron transfer with the structure to become adatoms rather than accept electrons directly from the electrode once a structure has begun growing. In embodiments where an electric field is used to promote nanostructure growth, the nanostructures grow outwards from edges of the electrodes but do not follow the electric field. It is noted that in prior work directed at nanowire assembly, such as directed electrochemical nanowire assembly (DENA), nanowires are assembled using an AC field but the nanowire assembly follows the electric field lines. Without wishing to be bound by theory, a possible reason for this difference, it is suggested herein, is that the present methods result in movement of the metal ions being a combination of diffusion and electrophoresis, rather than just electrophoresis alone in the DENA approach. The voltage applied in the present methods is sufficient to drive the reaction but not enough to completely dominate the motion of the metal ions.

Additionally, metallic nanostructures as described herein exhibit crown shyness, i.e., they avoid contact with neighbouring nanostructures, even those charged with the opposite polarity. Without wishing to be bound by theory, it is suggested herein that the crown shyness is due to surface properties of the nanostructures causing the nanostructures to repel each other at close range (e.g., sub-nanometer). Additionally, for nanostructures with the same charge, growth is in a lateral outward direction, where the metal ion concentration will be greatest. In the vicinity around the nanostructures there will be a depletion zone as metal ions are consumed. Thus, the nanostructures preferentially grow outward or towards areas without other nanostructures. When the nanostructures grow toward the opposite polarity (anode) there is a repulsive force from the anode which restricts the metal ions from reaching tips of the nanostructures. Since the metal ions can't reach the tips of the nanostructures, growth is halted, preventing contact.

As described herein, methods for preparing a sensor element nanostructure may comprise disposing at least two metal microelectrodes in a spaced relationship on, near, or in the vicinity of (e.g., within 100-1000 µm) a non-electrically conductive substrate such that a detection site is formed between opposing edges of the at least two microelectrodes. In one embodiment, the at least two microelectrodes are disposed on the surface of substrate. In another embodiment, at least one microelectrode of the at least two microelectrodes is disposed near the surface of the substrate, e.g., at least one microelectrode may be suspended above the surface of the substrate.

Embodiments include disposing a solution comprising a stabilizing agent and a metal salt on the substrate at the detection site; and applying an electrical signal comprising an alternating current (AC) to the at least two microelectrodes; wherein the electrical signal creates an AC electric field that induces, directs, and/or influences the metal salt to form the nanostructure on the surface of the substrate at edges of the at least two microelectrodes.

As used herein, the term "stabilizing agent" or "stabilizer" refers to an agent that provides one or more functions that enhances or facilitates metallic nanostructure growth. For example, a stabilizing agent may provide one or more of: acting as a metal complexing/capping agent (i.e., it exhibits preferential adsorption to metal crystal planes, and forms a neutral complex with metal ions in solution, thereby enhancing nanostructure formation and reducing the free metal ion concentration); acting as a supporting electrolyte (i.e., raising conductivity of the solution and reducing migration of metal ions ensuring the motion of metal ions is largely controlled by diffusion and not migration (electrophoresis)); and completing the electrical circuit between electrodes (i.e., it can be oxidized at an anode, resulting in transfer of electrons to the electrodes thereby completing the electrical circuit). Examples of stabilizing agents include, but are not limited to, citrate, carboxyl compounds such as succinate, trans-aconate, malonate, ionic surfactants such as sodium dodecyl sulfate (SDS), polymer chains such as polyvinyl pyrrolidone (PVP). Combinations of such stabilizing agents may also be used. The extent to which a stabilizing agent is incorporated into a metallic nanostructure may vary, depending on nanostructure growth conditions and the composition of the solution, i.e., the species of metal salt(s) and stabilizing agent(s) used. For example, in some embodiments the stabilizing agent may be present substantially only on the outer surface of the metallic nanostructure, with minimal or no incorporation as a building block in the nanostructure.

A substrate may have a surface property that is suitable for metal deposition (i.e., growth of metallic nanostructures including dendrites), and/or the surface of a substrate may be modified to achieve a property that is suitable for metal deposition. Such a suitable surface property may promote non-covalent adhesion (e.g., electrostatic, hydrogen bonding, Van der Waals force) of a metal to the surface, e.g., a suitable property may be a low surface energy. Modifying a property of the surface of the substrate may include oxidizing the surface and/or exposing the surface to a surface energy reducing agent, such as silane, an electrostatically charged molecule, and/or an agent that promotes adhesion of the metal to the substrate, e.g., a surface coating with a material such as graphene, a graphene derivative, liquid Teflon™, or physisorption of a surfactant such as a detergent onto the surface, which may include creating an island for attachment of the metal or creating a suitable charge on the substrate. The substrate may be of an electrically insulating material that provides an insulating surface with suitable surface properties for microstructure deposition, or that can be chemically modified to have such properties. For example, the substrate may be, but is not limited to, silicon ($SiO_2$) or a polymer material.

As described herein, a sensor element comprises a metallic nanostructure and a non-electrically conductive substrate. Embodiments may include at least two microelectrodes disposed on the substrate in a spaced relationship such that a detection site is formed between opposing edges of the at least two microelectrodes, wherein the metallic nanostructure is disposed at edges of the at least two microelectrodes.

The nanostructure may be a branched, clustered, aggregated, fractal, and/or dendritic structure, formed from a single metal, or a mix of two or more metals. The metal(s) may be selected from, but is (are) not limited to, silver, gold, copper, platinum, aluminum, gallium, indium, rhodium, an alkali metal such as lithium, sodium, potassium, rubidium, cesium, or a combination of one or more thereof. Thus, whereas embodiments are described herein with respect to silver nanostructures, the invention is not limited thereto.

One application for the methods and sensor elements is use as surface-enhanced Raman scattering (SERS) substrates. In other optical sensing applications, a sensor element may be used as a surface plasmon resonance (SPR) or a localized surface plasmon resonance (LSPR) platform. A sensor element may also be used in electroanalytical methods such as coulometry, amperometry, and voltammetry. Electrical-based sensing such as electrochemical sensing is another application for embodiments including electrodes, as the connection of nanostructures to the electrodes offers the potential for active capture of particles such as proteins, bacteria, viruses, and DNA strands with the use of an electric field. Thus, whereas applications of the sensor elements are described herein primarily with respect to SERS, it will be appreciated that there are many other applications.

Procedures

In the following sections, the materials and procedures used to fabricate sensor elements are described.

Materials

Silver nitrate, gold (III) chloride trihydrate, trichloro(1H,1H,2H,2H-perfluorooctyl)silane (FS), trisodium citrate, sodium succinate dibasic, trans-aconitic acid, sodium dodecyl sulfate (SDS), polyvinyl pyrrolidone (PVP, average MW 10 000 g/mol), melamine, rhodamine 6G (R6G), Coosmassie brilliant blue (BB), thiram, avidin-FITC and green fluorescent protein (1 mg/mL) were purchased from Sigma Aldrich (Oakville, ON, Canada). Polished silicon wafers (4" diameter) with a thermally grown SiO2 layer (0.5 µm) were purchased from University Wafer (South Boston, MA, USA). Millipore® water (18.2 MΩ cm) was used for prepare all aqueous solutions. A transparency-based photolithography mask was designed using AutoCad™ and printed by Advance Reproductions Corp. (North Andover, MA, USA). Tropicana™ apple juice was purchased from a local grocery store.

Microchip Fabrication

The microfabrication of electrodes was carried out at Nanofabrication Kingston (NFK, Innovation Park, Kingston, Ontario). The wafer was washed using a solvent wash (acetone, isopropanol, water) before being treated with oxygen plasma. A layer of the negative photoresist AZ nLOF 2020 (MicroChem Corp, Westborough, MA) was spun-coated onto the surface. The surface was then patterned using a photolithography mask aligner before being placed in a bath of AZ 300 MIF (MicroChem Corp, Westborough, MA) to develop. Metal deposition was done using physical vapour deposition with 5 nm of chromium deposited as an adhesive layer before 100 nm of gold was deposited. Remaining photoresist was removed using AZ 400T Resist Stripper (MicroChem Corp, Westborough, MA). The wafer was finally diced using a diamond tip scribe.

Surface Modification of Substrates

If the substrate has surface properties that do not inhibit nanostructure growth, or that promote nanostructure grow, then no surface modification may be required. However, a substrate with surface properties that repel rather than attract metal deposition and dendrites from the surface may inhibit nanostructure growth, and requires modification. For example, if the substrate has a high surface energy (e.g., 25 ergs/$cm^2$ or higher), or if the fabrication process results in a high surface energy, then modifications to alter the surface properties of the substrate and reduce the surface energy may be required. Examples of various approaches to modify the surface and reduce the surface energy are discussed above.

In the embodiments described herein, the electrodes were fabricated on silicon chips using a process which exposed them to high oxygen plasma levels. As a result, the surfaces had a high energy which would repel the dendrites away from the surface. To lower the surface energy, and change the interaction of dendrites and the substrate from a repulsive to an attractive nature, the chips were silanized to ensure a non-covalent attraction between the dendrites and the insulating surface. Chips were washed with acetone, ethanol, and then water before being dried. Silicon oxide on the chips was then activated by exposing the chips to plasma for 5 minutes. Afterwards the chips were placed in a vacuum chamber with 20 µL of FS overnight. Finally, the chips were washed again using dish soap along with the previous three solvents before being air-dried.

Such tuning of the surface properties of the silicon oxide substrate ensure they remain relatively constant and predictable, and promote interaction between the substrate and growing structure. Thus, as silver ions are reduced, the nanostructure grows out away from the electrode edge in a 2-dimensional direction rather than in a 3-dimensional direction.

Assembly of Nanostructures

Metallic nanostructures were formed using a two-electrode setup where the gold electrodes on the chip alternated as cathode and anode. BK Precision 4040B sweep function generator (Cole-Parmer Canada Inc.) was used to apply the electrical signal while a Tektonix 1002B oscilloscope was used to monitor the system. Approximately 10 μL of reactant solution was deposited on the centre of the chip before the electrical signal was applied for 10 minutes. The reactant solution typically consisted of a stabilizer (citrate, succinate, trans-aconitic acid, SDS or PVP) and silver nitrate. Concentration of either molecule was varied. The electrical signal used followed a sine function unless otherwise stated. Afterwards the chip was rinsed with water and air dried. Photos were taken using an Olympus microscope and D200 Nikon camera. A MLA 650 FED ESEM system was used to analyze the nanostructures via scanning electron microscopy (SEM). Fluorescent images were taken using an Olympus BX53 microscope with a Lumenera INFINITY 2 digital microscopy camera and X-Cite Series 120 Q Lumen Dynamics light source. All depositions were performed at room temperature.

Analyte Deposition

To evaluate the SERS performance of nanostructures formed under different conditions, R6G ($10^{-5}$ M) was allowed to adsorb onto the surface for 10 minutes before the droplet (10 μL) was removed. For calibration curves, both R6G and BB were drop casted onto the surface. Similarly, melamine and thiram spiked apple juice were deposited onto the surface and allowed to dry. Apple juice samples were found to gel over time, a gentle rinse with water was used to remove the gel after deposition. Protein capture using an electric field was performed using a 10 kHz, 15 Vpp signal for 15 minutes.

Raman Measurements

All spectra were recorded using either a Horiba/Jobin Yvon Raman (LabRAM) with a 632.8 nm He/Ne laser (17 mW), 1800 1/nm grating and an Olympus BX-41 microscope system or Ocean Optic Micro Raman (633 nm, 23.4 mW) system. Experiments involving different parameters of the dendrite formation were performed using the Ocean Optics Micro Ra-man system. The Horiba Raman system was used to test different analytes and different concentrations of R6G and BB. All spectra shown are an average taken from 10 different locations on a single chip. Data Processing was performed using Matlab (R2018a). Spectra were filtered using a Savizky-Golay filter before being baseline corrected [23]. Following SERS measurements, the nanostructures and analyte were removed using a cotton swap which had been soaked in dish soap. Chips were then washed with acetone, ethanol and water before being air dried and stored for reuse.

Parameters

In the following sections, parameters that induce, direct, and/or influence one or more of deposition, growth, and morphology of nanostructures are described. For simplicity, all solutions are described with the stabilizer concentration first and then the silver nitrate concentration (ex. 2 mM trisodium citrate with 0.5 mM of silver nitrate will be referred to as 2/0.5 mM solution). All initial results reported were obtained using citrate as a stabilizer.

Applied Voltage

Figure 1K:
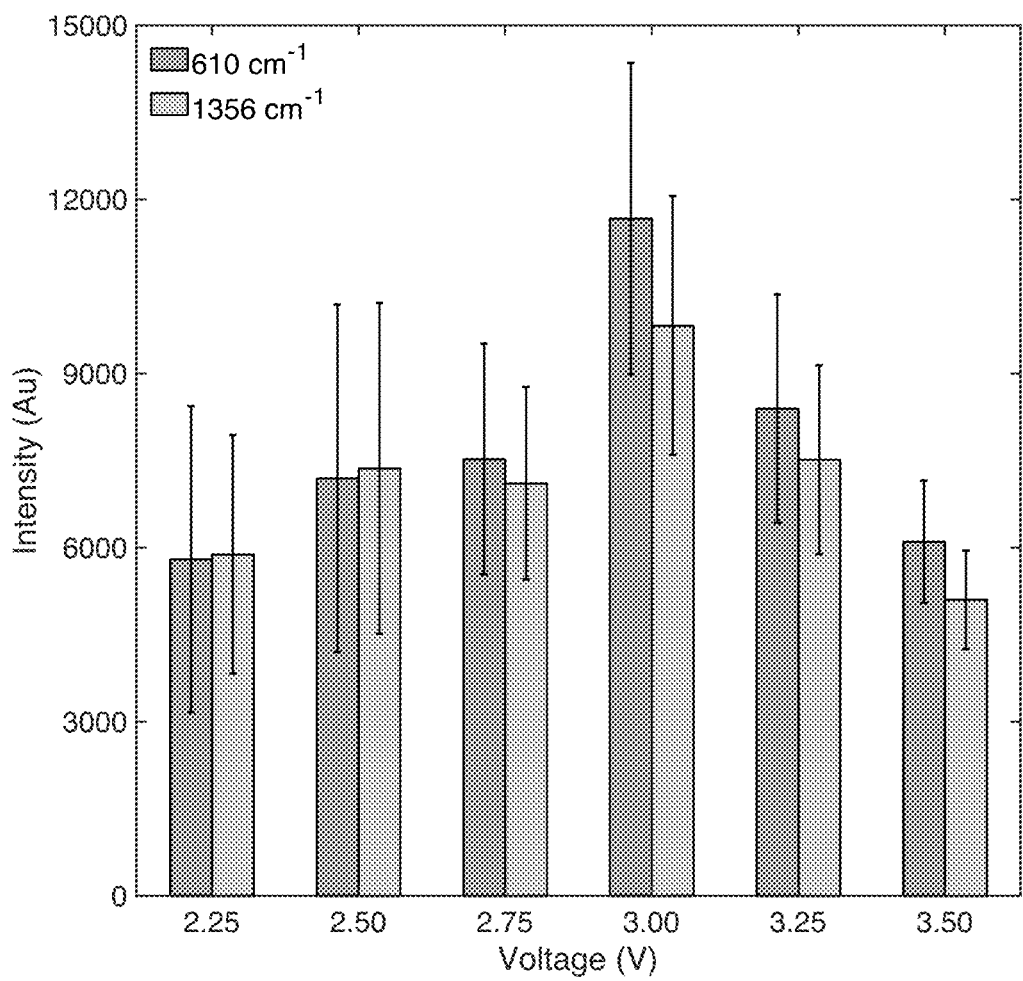
FIG. 1K is a plot showing average Raman intensity of two R6G peaks obtained from silver nanostructures formed at six different voltages; error bars indicate standard deviation.

A 2/0.5 mM solution was used with an AC electrical signal (sine wave) at a frequency of 10 Hz. As shown in the photomicrographs of FIG. 1, the applied voltage had a significant effect on the morphology of the nanostructures formed. At 0.8 Vpp no deposition occurred. At 0.9 Vpp, deposition occurred with tentacle-like aggregates forming randomly along the edge of the electrodes (FIG. 1A, panel A). Increasing the voltage to 1.00 Vpp or 1.25 Vpp increased the density and size of the aggregates (FIG. 1A, panels B, C). At 1.50 Vpp, the deposition began to form a dendritic nanostructure with a red tinge (FIG. 1A, panel D). Repeated testing found that one electrode had significantly more deposition than the other electrode. Without wishing to be bound by theory, it is suggested that this may due to the potential being near a transition voltage and due to differences in electrical resistance from the experimental setup, wherein one electrode is above the transition voltage while the other below it. At 1.75 Vpp and 2.00 Vpp, the dendritic nanostructures grew along edges of both electrodes in a similar manner (FIG. 1A, panels E, F). A second transition voltage was reached at 2.25 Vpp with a denser dendritic nanostructure and a different reddish tint (FIG. 1A, panel G). As the voltage increased to 2.50 Vpp, 3.00 Vpp, and 3.50 Vpp (FIG. 1A, panels H, I, and J, respectively) only slight changes in the colour of the nanostructures were observed though the rate of growth for the nanostructures increased. Examining the nanostructures assembled at 2.5, 2.75, 3.0, 3.25, and 3.5 Vpp revealed a denser nanostructure.

SEM showed that the nanostructures had regions of different morphology. Near the electrodes a much higher density of coverage was achieved and further away from the electrodes the nanostructures became more branched and wire-like. As the voltage increased, the region of higher density extended out further from the electrodes. Interestingly, at the higher voltages tested (>2.5 Vpp) these regions appeared particulate, wherein rather than having dendritic branches made from wires the dendrites consisted of particles. It is suggested that with a stabilizing agent such as citrate guiding the assembly and with a high enough overpotential/AC field, a secondary nucleation occurs on the tips of the nanostructures as they grow, or the start/stop from the AC field changes the concentration gradient around the particles thereby changing the growth mechanism.

Testing of the nanostructures found all structures formed at 2.25 Vpp and higher were SERS active. As shown in FIG. 1B, which is a plot of average intensity of two R6G peaks, SERS activity was relatively constant for six voltages (2.25-3.5 Vpp) though the higher voltages produced a larger surface coverage and thus made it easier to aim the Raman laser. 3.00 Vpp was found to have the optimal signal which is likely because of the high density of surface coverage and balance between different morphologies in the nanostructure.

Electrical Signal

The electric field used for deposition of a nanostructure may be established by controlling or adjusting one or more parameters (e.g., voltage, current, frequency, shape of waveform (e.g., sine, square, triangular, sawtooth, etc.), duty cycle) of the AC current, and optionally providing a DC offset or bias (described below), to thereby adjust the electric field.

For example, switching from a sine function to a square wave resulted in greater deposition. This was expected as current is responsible for the reduction of silver ions and is proportional to the voltage applied. Moving to a step function results in the total voltage input into the system increasing by a factor of 2*π (~6.28.) over the course of a single cycle. In addition, the step function applies the voltage at a constant max value rather than a constantly changing value, so that conditions for deposition are more intense using the step function rather than a sine function. A possible drawback of using a step function is that it is more damaging to the electrodes, reducing the number of times they can be washed and reused.

DC Bias

The inclusion of a DC bias in the electrical signal was found to alter the nanostructure deposition. Increasing the bias resulted in larger nanostructures forming on the more negatively charged electrode. The increased bias also limited growth on the positively charged electrode, with a 500 mV bias nearly eliminating any deposition on the positive electrode. These differences are likely due to the bias leading to one electrode generating a larger electrophoretic force on the silver ions and also operating above the minimal voltage required for deposition. Thus more reactants are pulled towards the negative electrode and the electrode can readily transfer an electron to the ions unlike the positive electrode.

While the DC bias was found to greatly impact the dendritic nanostructures formed, there were limited differences between the nanostructures in regard to SERS activity. All the nanostructures formed using a DC bias performed similarly. They did however outperform structures formed at the same conditions without a DC bias present. It is suggested herein that the DC bias generates more hotspots in the nanostructure for SERS enhancement.

Frequency

The frequency of the AC field may be used as a parameter for controlling nanostructure deposition. It was found that lowering the frequency lowered the density of the structures formed, while increasing the frequency too high could inhibit deposition. As the frequency is lowered, the deposition approaches DC conditions but due to the electrode design and presence of citrate deposition was still limited to the edges of the electrodes. The porous nature of the structures at lower frequencies is likely caused by the growth phase of the structures being continuous (limiting nucleation of new sites) and the lack for fluid to replenish the areas around the structures. A decrease in deposition at 100 Hz and higher is believed to be caused by the increase in electrically driven fluid flows and the reduced time for electron transfer between the electrodes and silver ions. Without sufficient time for electron transfer, not enough ions are transformed to form adatoms and a minimal number of adatoms are required to form a stable nucleus. The minimal number of adatoms for a stable nucleus likely increases with increased fluid flow. Thus, less nucleation sites are formed and those formed grow at a reduced rate. From the results three possible regions were identified where the morphology changes based on the frequency of the AC field applied: less than 0.10 Hz, between 0.10 and 10 Hz, and greater than 10 Hz. Initial microscopy revealed that lowering the frequency resulted in less 'jagged' nanostructures.

Deposition videotaped at the lowest frequency (0.01 Hz) confirmed that assembly only occurred on a single electrode at a time. Based on this and the results from the DC bias it is concluded that, like all electrolytic depositions, the nanostructures grow on the cathode only. However, due to the AC field, each electrode alternately acts as the cathode and the anode, and thus nanostructures can be formed on both electrodes without physically changing the connections to the electrodes.

In terms of SERS activity, the signal increased when the frequency was raised from 0.01 Hz and remained steady for the majority of frequencies that resulted in deposition. A frequency of 10 Hz was found to result in the smallest standard deviation and thus it was used for later testing.

Ratio of Citrate to Silver Nitrate

The stabilizer concentration was changed (0.05, 0.1, 0.5, 1.0, 2.0, 3.0, 4.0, 5.0, 10, 100, and 450 mM) while keeping the concentration of silver nitrate (0.5 mM) and deposition conditions fixed. Low concentrations of citrate result in nanostructures similar to electrodeposition without a stabilizer present; a thin layer of structures form on the edges of the electrodes. As the concentration of citrate is increased from 0.5:1 ratio to a 4:1 ratio with respect to the concentration of silver nitrate, the nanostructure morphology changes and the structures grow outwards from the electrode surface, highlighting the importance of using a stabilizer such as citrate to guide the growth of the structures. Above a 3.0 mM concentration (6:1 ratio), nanostructure growth was slowed and fully inhibited at 100 mM. It is suggested that the inhibition is caused by two mechanisms: 1) citrate, while it has preferential adsorption to silver crystal planes, binds to all crystal planes and at high concentrations likely outcompetes any silver ions attempting to approach the surface; and 2) citrate and silver ions form a neutral complex in solution thereby reducing the free silver ion concentration.

The intermediate concentrations of citrate (0.5, 1.0, 2.0, 3.0, 4.0, 5.0, 10 mM) were all found to produce SERS active nanostructures. A 4:1 ratio between citrate and silver nitrate was found to produce the highest intensity and was selected as the standard ratio to use for future experiments.

Total Ions

Maintaining a 4:1 ratio between citrate and silver nitrate, various concentrations of citrate:silver nitrate were tested at 2.5 Vpp, 10 Hz. At low concentrations, a reddish-gold nanostructure was assembled. As the concentration increased, the nanostructure became darker (denser with additional layers forming) and began to grow more in a 3-dimensional path, outwards from the edges and surfaces of the electrodes. The highest concentration tested (10 mM citrate:2.5 mM silver nitrate) had structures which fell off during the drying process after formation. The increase in total reactants present along with change in solvent conductivity likely contributed to the changes in the nanostructure formed.

The SERS activity of the nanostructures tested was found to increase as the total ion concentration increased. The increase in surface coverage likely resulted in more hotspots being formed and thus an increase in the SERS signal. The lack of stability from structures formed at higher concentrations along with risk of damaging the electrodes suggest that total ion concentration should be kept at or below 4 mM citrate:1 mM silver nitrate solution.

Different Electrode Designs

Figures 2A, 2B, 2C, 2D, 2E, 2F, 2G, 2H:
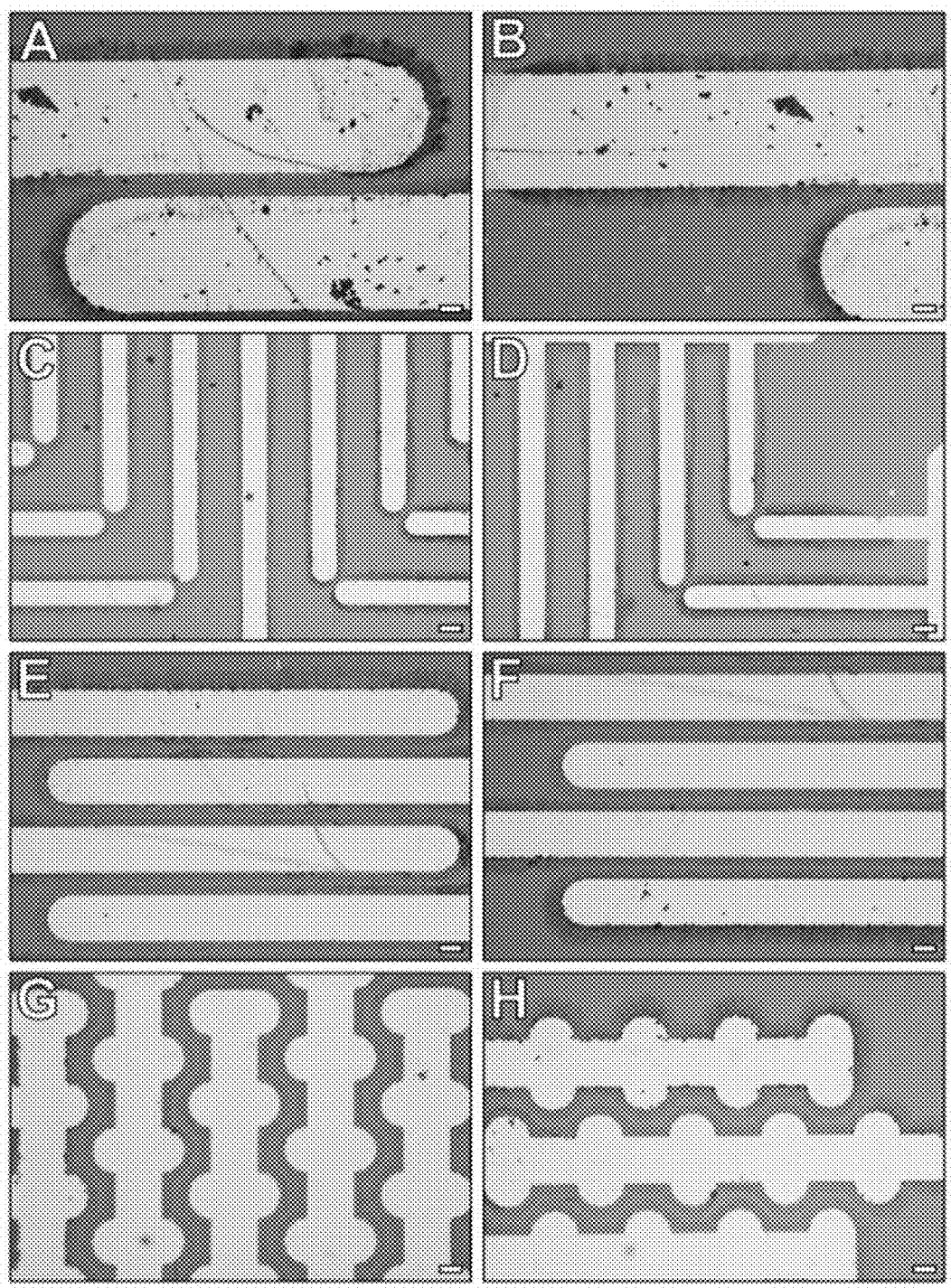
FIGS. 2A-2H are photomicrographs showing electrode patterns used with a 2/0.5 mM solution and a voltage of 2.5 Vpp at 10 Hz.
Figures 3A, 3B, 3C, 3D, 3E, 3F:
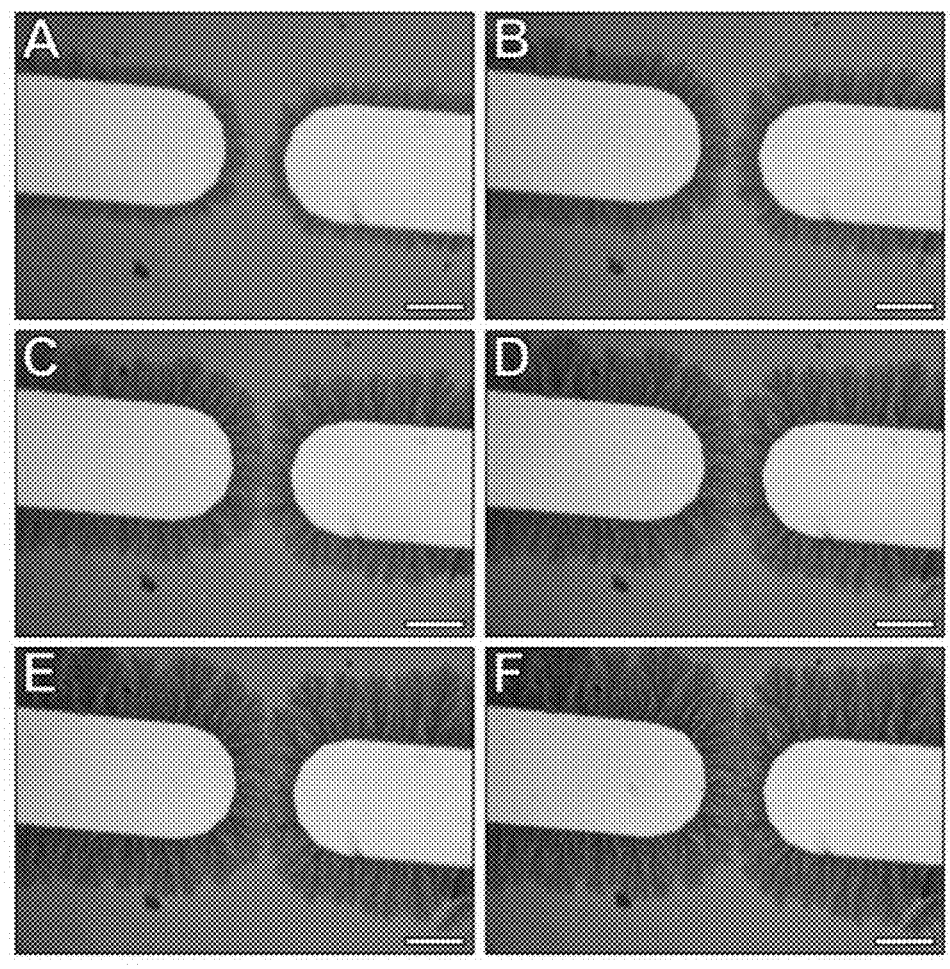
FIGS. 3A-3F are photomicrographs showing growth of nanostructures over durations from 10 minutes (FIG. 3A) to 15, 20, 25, 30, and 35 minutes (FIGS. 3B-3F, respectively), using a voltage of 2.5 Vpp, frequency of 0.5 Hz, and 2/0.5 mM solution (scale bar is 100 microns).

The nanostructure deposition technique can be applied to a variety of electrode platforms with designs ranging from interdigitated electrodes (e.g., 2-8 fingers with minimal 100 micron separation) to a multipole design with, e.g., a minimum 40 micron gap. FIGS. 2A-2H show non-limiting examples of different designs that were tested. In all designs tested, deposition was limited to edges of the electrodes and all regions of the electrodes in contact with the solution had dendritic nanostructures growing outwardly from the edges of the electrodes (SEM revealed micron-size gaps between structures, suggesting Volmer-Weber growth and not Stranski-Krastanov growth (Z. Xi, et al., 2018). FIGS. 2A and 2B show an overlay design with a minimal gap of 100 μm, FIGS. 2C and 2D show a multipolar design with a minimal gap of 40 μm; FIGS. 2E and 2F show an interdigitated design with a minimal gap of 100 μm, and FIGS. 2G and 2H show a "dogbone" design with a minimal gap of 100 μm.

It was observed that the nanostructures grow towards one another but growth slows and appears to stall when the structures approach one another, leaving a gap. It was found that the gap could be closed, i.e., the structures caused to grow towards one another and touch, by increasing the voltage. It is possible that the concentration of ions in the gap is at such a state that the reaction stalls. This may be caused by the concentration of silver ions being too low in this region, or the concentration of citrate in this region being high enough to hinder the reaction. Given the nature of citrate adsorbing and desorbing from the nanostructure surface as the electrode shifts from positive to negative phase, it is likely that in the narrow gaps the released citrate molecule interacts with the silver ion before the silver ion can reach the surface.

A major benefit of hindered growth in the gap is that it removes the risk of an electrical short-circuit. If the nanostructures come into contact with one another, a complete circuit would be made and the electrode could be damaged beyond use almost immediately. Under conditions described herein, the only way for shorting to occur is if a conducting island is formed, and two nanostructures growing from opposing electrodes to come into contact with the conducting island at approximately the same time. However, if a structure growing from one electrode reaches the island with time to form dendrites around the island, then an approaching structure from an opposing electrode will not touch the island.

The nanostructures tested (FIGS. 2A-2H) all had SERS activity. In general, performance of the designs with larger electrode/nanostructure area was not as good as the designs with smaller electrode/nanostructure area. This is likely due to all nanostructures being made under the same conditions with the same amount of reactant solution. For the larger structures, since more structures are being formed, the density of the structures is reduced resulting in fewer hotspots available for SERS enhancement. Thus while the same electrical parameters and solution composition can be used for different electrode designs, the volume of solution should be scaled to match the microelectrode area.

Extended Surfaces

In all embodiments shown thus far, nanostructures were grown for a duration of 10 minutes. Allowing the deposition to continue for a longer duration allows continued growth of the dendritic structures. The photomicrographs of FIGS. 3A-3F show growth of nanostructures over durations of 10 minutes (FIG. 3A) to 35 minutes (FIG. 3F), using a voltage of 2.5 Vpp, frequency of 0.5 Hz, and 2/0.5 mM solution (scale bar is 100 µm). This demonstrates the potential for the technique to be used to make large scale areas compatible with fiber optic-based Raman devices. As the dendrites grew they took on a different morphology. This is likely caused by either changes in the solution composition (silver ions concentration depleted) or electrical losses in dendrites beyond 100 microns causing the overpotential to decrease at those regions. The rate of nanostructure growth may be controlled by varying droplet size or by using multiple droplets (i.e., more solution). In some embodiments a multidroplet approach may be used to optimize dendrite growth and control the gap. For example, a rate of one drop/minute may be used to maintain dendrite growth at about 10 microns/minute. In some embodiments nanostructure growth may be carried out with an abundance of solution, for example, the microelectrodes may be immersed in a reservoir containing an abundance of solution.

Stabilizing Agent

All embodiments described thus far use citrate as the stabilizing agent. However, other stabilizing agents, and combinations of stabilizing agents, may be used to guide the deposition of silver to make nanostructures, with appropriate adjustment of the solution composition. Adjustment is required since each stabilizing agent interacts with silver or other metal(s) (ions and solid) differently; for example, with varying interaction energies depending on which plane it is interacting with.

Figure 4A:
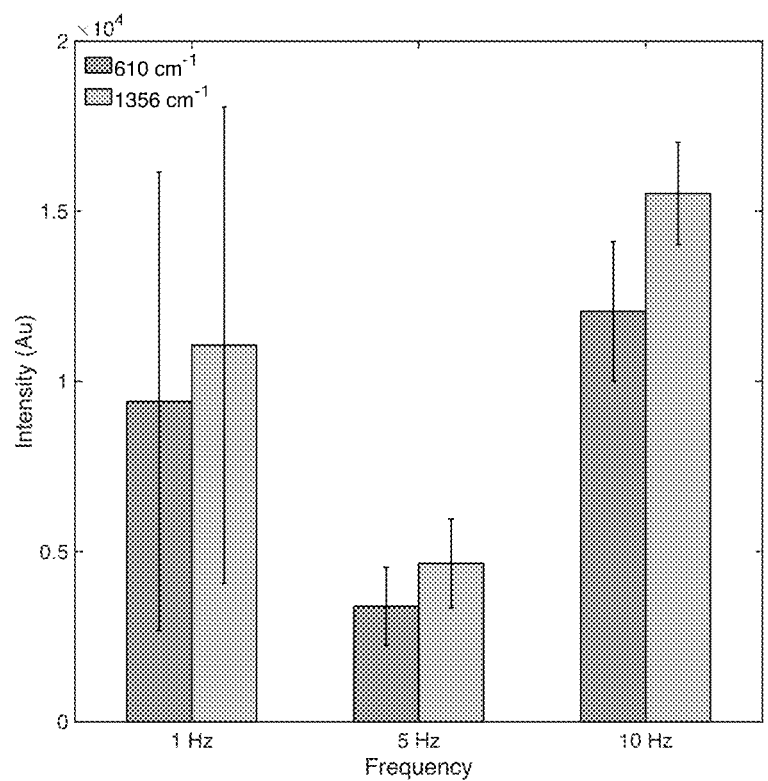
FIGS. 4A and 4B are plots showing average intensity of two R6G peaks obtained from silver nanostructures formed (4A) at different frequencies using succinate as the stabilizing agent; and (4B) at different frequencies and concentrations using trans-aconate as the stabilizing agent; error bars indicate standard deviation.
Figure 4B:
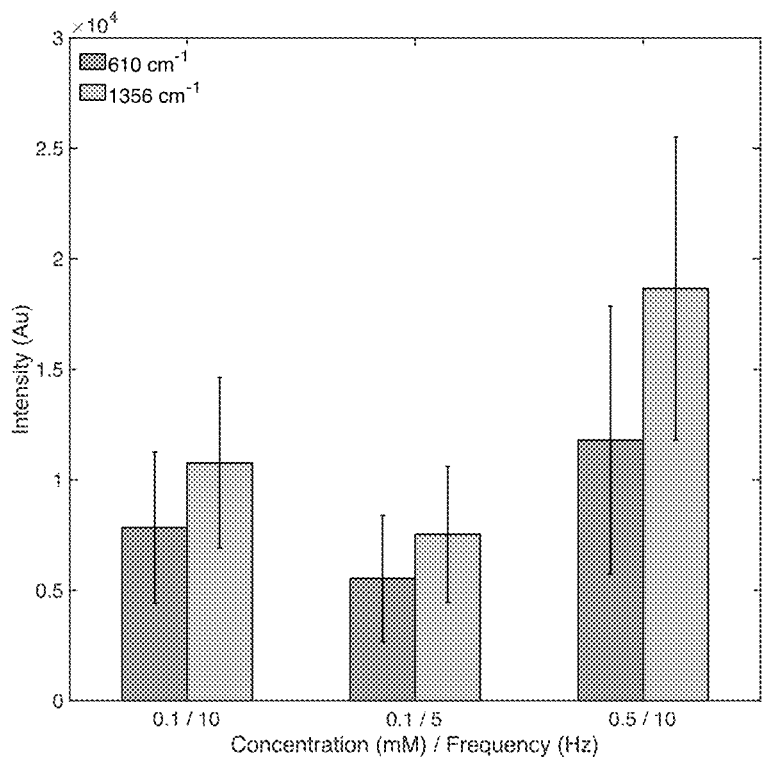

Structures were formed using the carboxyl compounds succinate and trans-aconate. For succinate, nanostructures were formed at 3 Vpp using a 2/0.5 mM solution of succinate:silver with frequency of 10 Hz and 15 minute deposition time, 5 Hz and 10 minute deposition time, and 1 Hz and 10 minute deposition time. For trans-aconate, structures were formed at 2.5 Vpp for 10 minutes with 0.5 mM silver nitrate solution with 0.1 mM aconate at 10 Hz, 0.1 mM aconate at 5 Hz, and 0.5 mM aconate at 10 Hz. All nanostructures were visually different from each other and from those formed with citrate, exhibiting differences in structural morphology. SERS activity for these structures was high, as shown in the plots of average intensity of two R6G peaks (FIG. 4A, succinate; FIG. 4B, trans-aconate), with some combinations of solution composition and electrical parameters outperforming citrate-based structures. Malonate, another carboxyl compound, was also tested but no solution composition/electrical parameter combination used resulted in deposition.

Figure 5A:
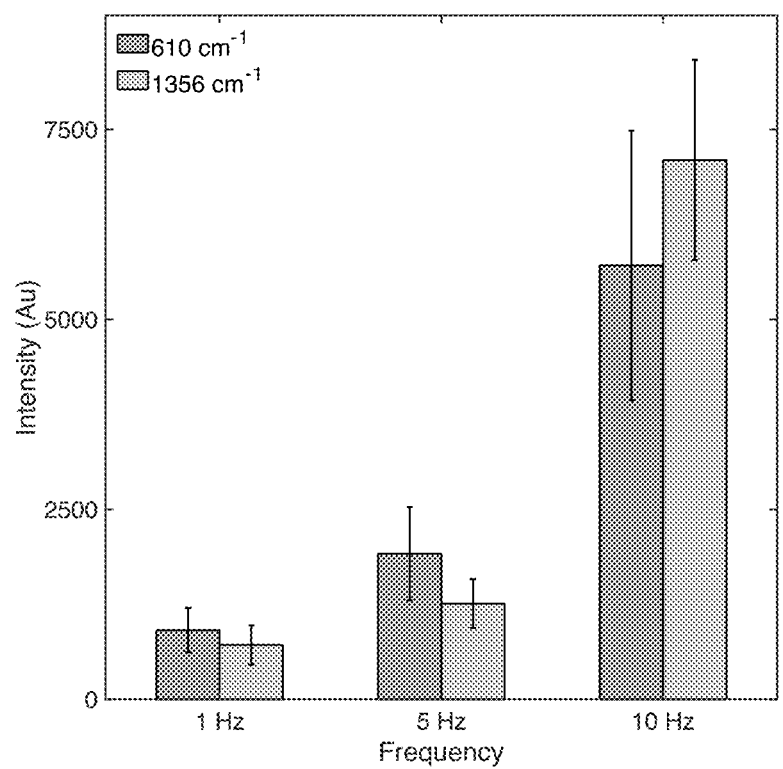
FIGS. 5A and 5B are plots showing average intensity of two R6G peaks obtained from silver nanostructures formed (5A) at different frequencies using sodium dodecyl sulfate (SDS) as the stabilizing agent; and (5B) without poly-vinyl-pyrrolidone (PVP) present (SN 3.0 Vpp and SN 2.5 Vpp) and with PVP (right-most bars); error bars indicate standard deviation.
Figure 5B:
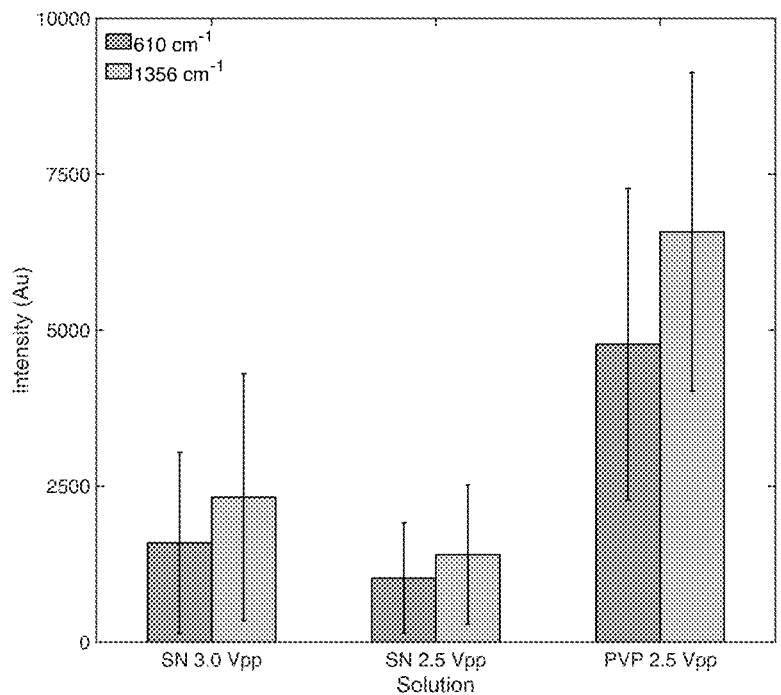

SDS (an ionic surfactant) and PVP (a large polymer chain) were also used as stabilizing agents and required a lower concentration/ratio than citrate for deposition to occur. For SDS, nanostructures were formed using a 0.5/0.5 mM solution with a voltage of 2.5 Vpp at 1 Hz, 5 Hz, and 10 Hz. For PVP, structures were formed at 2.5 Vpp, 10 Hz, with 0.5 mM silver nitrate used for all 10 minute depositions, with 2.0 mM PVP, 0.1 mM PVP, and 0.05 mM PVP. The lower stabilizer concentration is likely due to SDS and PVP being larger molecules than the carboxyl molecules, resulting in a slower desorption from the silver nanostructure during the negative phase. PVP in particular has multiple sites for adsorbing to silver and thus is likely to inhibit any growth of nucleus sites at high to moderate concentrations. Based on the nanostructures formed, it is suggested that SDS and PVP were more likely to be incorporated into the structures; which would explain why the SERS activity of these structures was relatively weak compared to structures formed using carboxyl compounds. FIGS. 5A and 5B are plots showing average intensity of two R6G peaks obtained from silver nanostructures formed (FIG. 5A) at different frequencies using SDS as the stabilizing agent; and (FIG. 5B, right-most bars) using PVP at 0.05 mM (error bars indicate standard deviation).

As a control to demonstrate the importance of using a stabilizer, nanostructures were made without a stabilizing agent present. A 0.5 mM silver nitrate solution was used without any stabilizer, at 2.5 Vpp, 10 Hz, 10 minute deposition time and at 3 Vpp, 1 Hz, 15 minute deposition time. At 10 Hz the nanostructure was formed only at the tips of the electrodes. At the lower frequency of 1 Hz the structure covered a larger area but still lacked a consistent morphology. It is concluded from these results that a stabilizer is required to guide the deposition of silver to ensure a well-defined structure is formed. It is suggested that without a stabilizer, silver ions are able to interact with all existing crystal planes equally, thus a dense 3-dimensional silver nanostructure is formed but it lacks nano-features. The SERS activity for nanostructures made without a stabilizer was weak (FIG. 5B, SN 3.0 Vpp and SN 2.5 Vpp).

Functionalized Nanostructure

Additionally, or alternatively, nanostructures may be functionalized with, for example, one or more of a protein (e.g., enzyme, antibody), antibody fragment (e.g., an epitope), nucleic acid (e.g., RNA, DNA, aptamer), or functional molecule (e.g., a self-assembled monolayer (SAM) comprising hydrocarbon tails terminating at two functional groups, one group on either side of the chain), including combinations thereof, in order to optimize specificity and sensitivity for a selected analyte. For example, a nanostructure may be prepared that projects certain surface functional groups, to assist in the coupling of an analyte with the nanostructure. Surface modification/functionalization may include application of a carbon-based material such as graphene and graphene derivatives to a nanostructure. For example, graphene oxide, reduced graphene oxide, or multilayer graphene particles may be deposited on the nanostructure to increase the SERS signal. Graphene materials may be deposited as a coating by, e.g., spraying or otherwise applying a suspension of graphene-based nanoplatelets directly on the surface of the nanostructure (e.g., by applying the coating first, and then forming the nanostructure on top of the coating). Functionalized nanostructures enhance SERS detection of an analyte by binding to the analyte and concentrating it at the detection site. Functionalized nanostructures may be used alone or together with an electric field (i.e., active capture, as described below) to concentrate the analyte at the detection site.

Mechanism for Deposition

Without wishing to be bound by theory, it is suggested that the electrolytic deposition of silver ions into nano-featured structures begins with ions being attracted to the edge of the electrode acting as a cathode (negatively charged), the edge having the highest electric field strength. Electron transfer occurs between the silver ions and the cathode resulting in the ions becoming adatoms on the surface of the cathode (focused near edge of electrode). The adatoms diffuse along surface of electrode edge until a stable nucleation site is formed (reached when n number of adatoms come together). Electro-osmosis driven flows on the top surface of the electrode likely limits adatoms becoming stable nucleation sites in that region.

Nucleation sites on the edge of the electrode act as nano-extensions to the electrode. The electric field is highest at these points resulting in silver ions to be attracted to these areas more so than the edge of the electrode. As the silver ions approach the nuclei, a direct electron transfer occurs between the nuclei and the ions resulting in adatoms being added to the nuclei directly. As the nuclei grows into a structure, it comes into contact with the substrate (silicon oxide) surface, due to the structure and substrate having complimentary surface properties, the interaction between the two is promoted (attraction, $\Delta G_{132}$ (lo)<0) and thus the structure adsorbs to the surface, essentially anchoring growth of the structure parallel to the substrate. The silicon oxide, due to its insulating properties, also helps to distort the electric field and thus may contribute to the flux ions to the growing structures.

Growth of the nanostructures shows individual stems extending from the electrode edge. (Growth of the nanostructures starts as stems from which branches grow, referred to as dendrites.) The stems appear to be discrete from one another with growth between adjacent stems not resulting in the stems touching. Thus, in appearance the growth resembles Volmer-Weber growth mode. Beyond visual inspection, the surface energy of the interfaces between silver (s), gold (g) and the solution (aq) can be used to predict the growth mode. For Volmer-Weber growth, $\gamma_{g-aq} \leq \gamma_{s-aq} + \gamma_{g-s}$ must be true (where y indicates surface energy).

When the voltage switches from a negative value to a positive value, growth halts and silver ions are repelled away from the surface. Citrate is attracted to the surface and adsorbs to the surface and due to different binding preferences the adsorption will not be equal on each of the silver planes. During this time, the citrate may also be undergoing oxidation on the surface of the structure acting as an anode (positively charged).

When the voltage returns to a negative value, the citrate is repelled off the surface while silver ions are attracted to the surface. Due to the difference in binding affinities, not all the silver planes are exposed at the same time and as a result different planes grow father than others. Given that citrate prefers binding to the Ag(111) plane, the Ag(100) and Ag(110) planes should be the planes that experience growth.

As long as the voltage losses in the silver structure do not accumulate too high and the concentration of silver or ratio of silver:stabilizer does not drop too low, the cycle of growth starting and stopping will continue. The combination of a concentration gradient of silver around the growing tips and stabilizers with different binding preferences to silver result in dendritic/nanowire growth.

If the voltage is too low then the necessary overpotential needed to overcome the activation energy for silver reduction is not met and no deposition will occur. As the voltage increases, growth switches from kinetic control to diffusion control. At diffusion control the silver ion is reduced as soon as it reaches the surface, thus dendritic and nanowire structures are formed.

If the frequency of the applied field is too high (e.g., greater than 500 Hz), the oscillation of the electrode between cathode and anode is too fast, limiting the formation of stable nucleation sites. The higher frequency reduces the ability of electrophoresis to attract silver ions from the bulk solution and the adatoms formed may be removed before forming a stable nucleus due to the increase in electro-osmotic flows.

If the surface properties of the substrate and structure are not complementary and there is a net repulsion between the two ($\Delta G^T_{132}$(lo)>0), the structure grows in a 3-dimensional direction from the edge of the electrode. The lack of anchoring to the substrate results in the nanostructure releasing from the electrode when dried.

Analyte Detection

Figure 6:
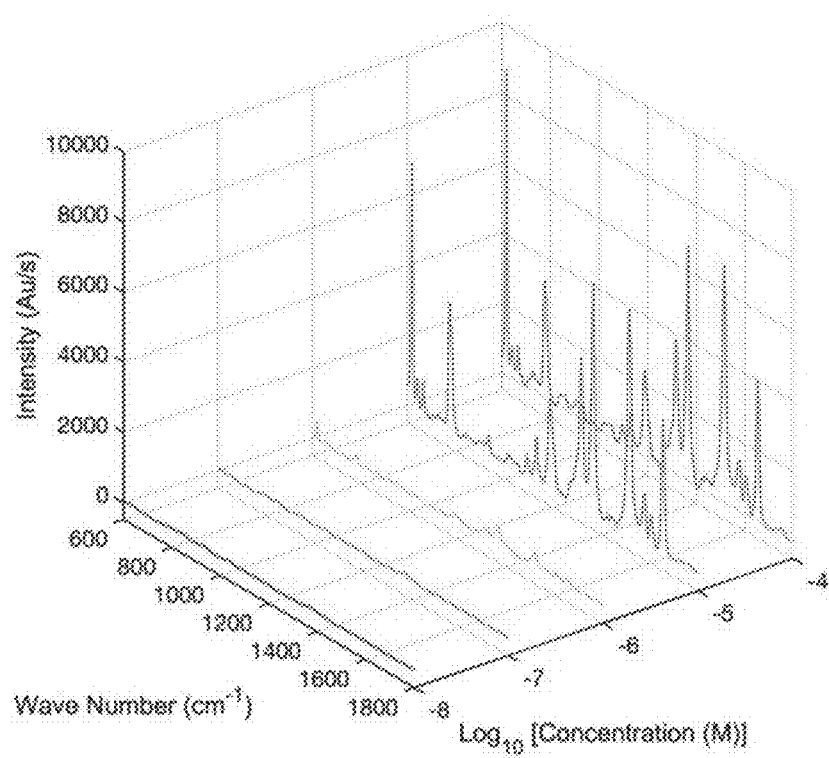
FIG. 6 is a plot showing the SERS signal obtained for RG6 at various concentrations, using a sensor element according to one embodiment; wherein 12 spots were averaged for each concentration.
Figure 7:
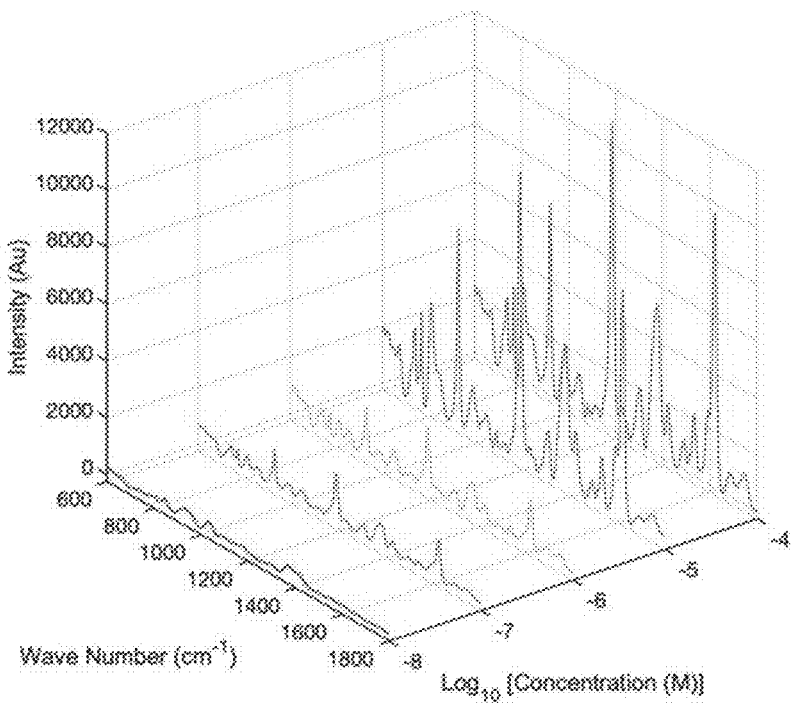
FIG. 7 shows the SERS signal obtained for Coomassie brilliant blue (BB) at various concentrations, using a sensor element according to one embodiment, wherein 12 spots were averaged for each concentration.

Four different analytes were tested using sensor elements with nanostructures assembled at 3 Vpp, 10 Hz, using a 4/1 mM solution: R6G, BBR, melamine, and thiram. Both R6G and BBR were detected over a range of techniques (FIG. 6 and FIG. 7). Melamine in water could easily be detected at 1 ppm and 100 ppb (FIG. 8) while thiram was detected at 1 ppm in apple juice without any preprocessing of sample (FIG. 9).

FIGS. 6 and 7 show the SERS signals obtained for R6G and BBR, respectively, at various concentrations, with Horiba Raman settings ×10 objective, 1.7 mW laser, 5 averages each with a 6 second acquisition time. 12 spots were averaged for each concentration.

Figure 8:
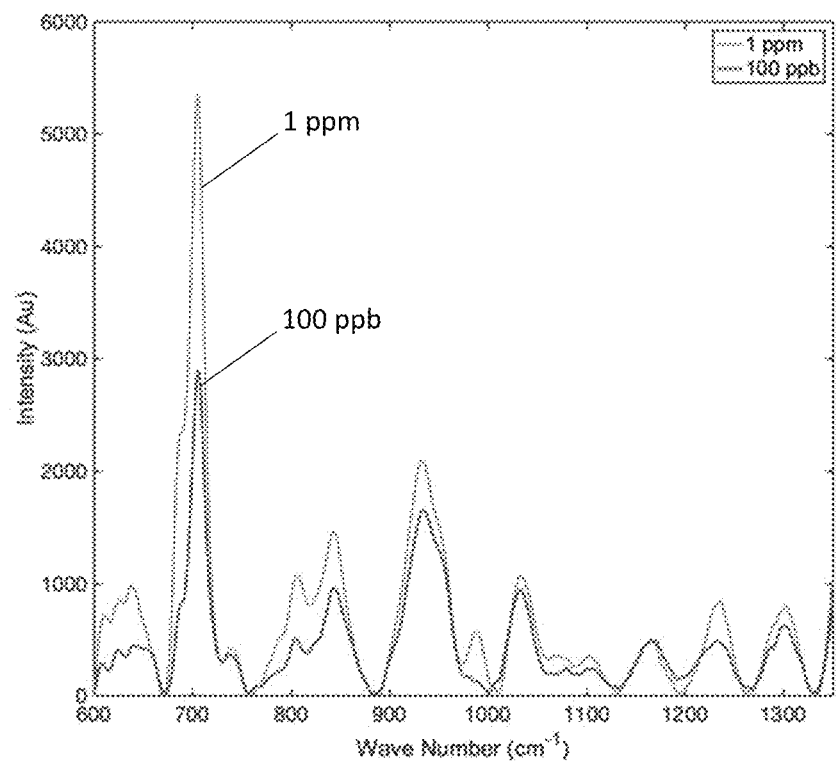
FIG. 8 shows the SERS signal obtained for melamine in water at 1 ppm and 100 ppb, using a sensor element according to one embodiment, wherein 10 spots were averaged for each concentration.

FIG. 8 shows the SERS signal obtained for melamine in water at 1 ppm and 100 ppb, with 17 mW laser, 5 averages each with a 2 second acquisition time. 10 spots were averaged for each concentration.

Figure 9:
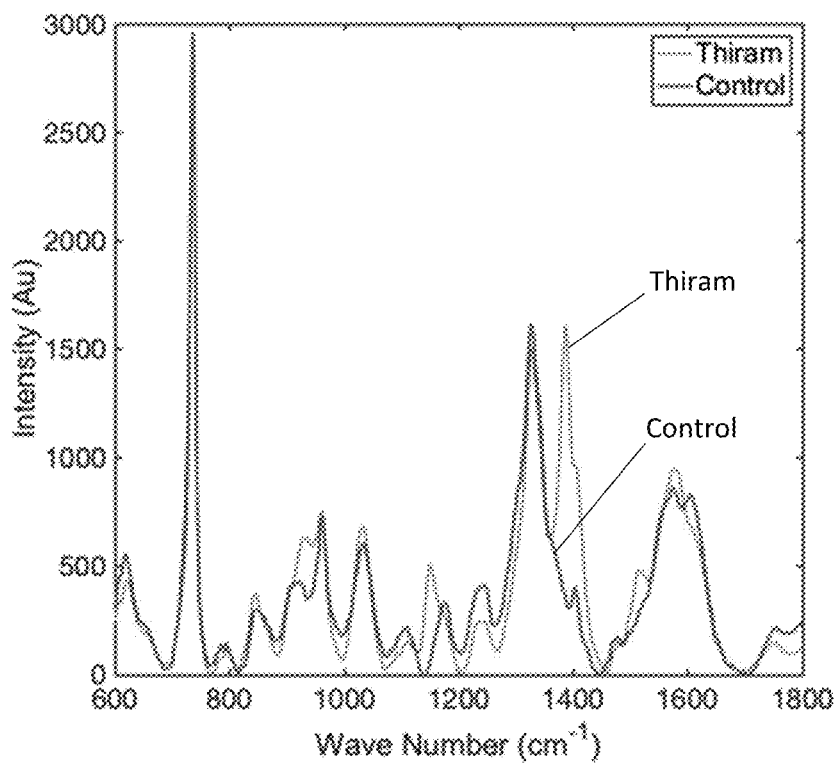
FIG. 9 shows the SERS signal obtained for apple juice and apple juice spiked with 1 ppm thiram, using a sensor element according to one embodiment, wherein 10 spots were averaged for each concentration.

FIG. 9 shows the SERS signal obtained for apple juice and apple juice spiked with 1 ppm thiram, with 17 mW laser, 5 averages each with a 2 second acquisition time. 10 spots were averaged for each concentration.

Active Capture

Figures 10A, 10B, 10C, 10D, 10E, 10F:
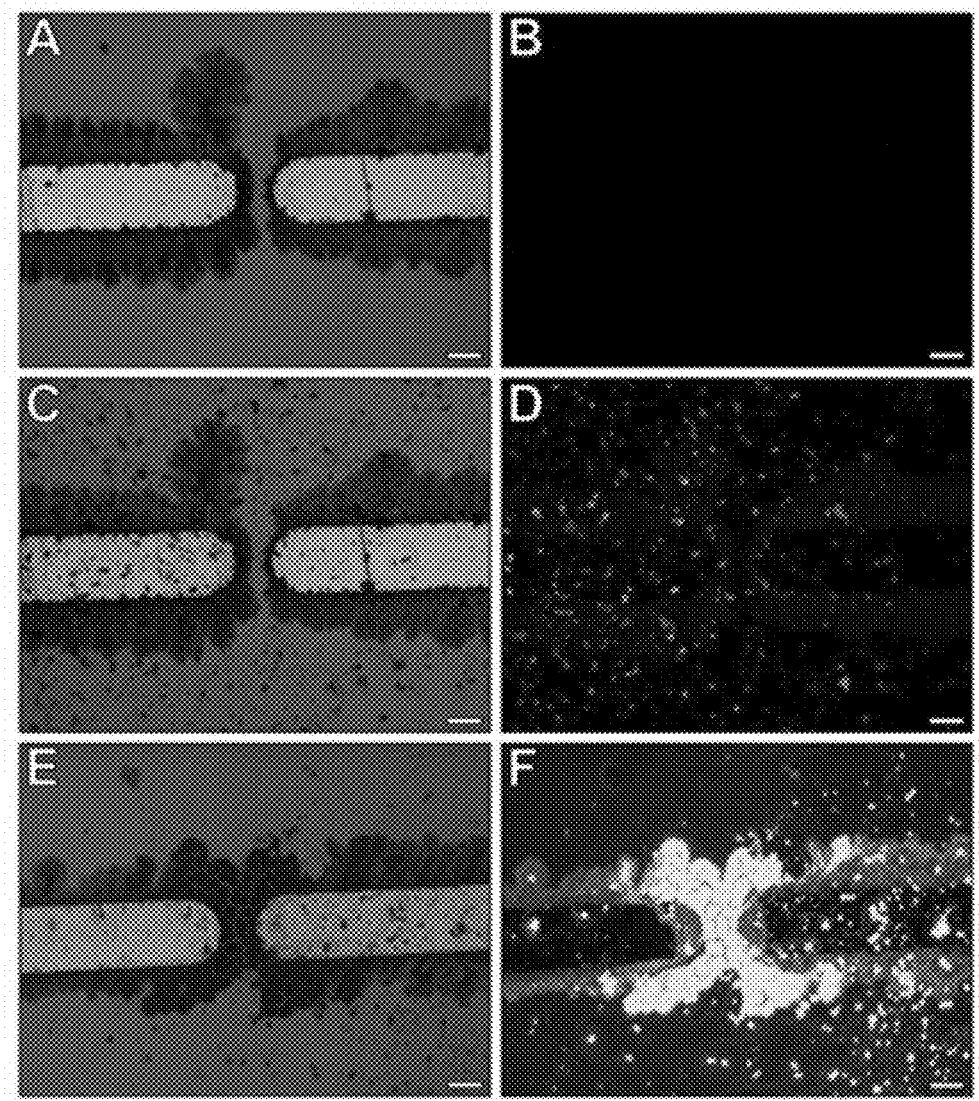
FIGS. 10A-10F is a series of photomicrographs showing adsorption of fluorescein isothiocyanate (FITC)-avidin with and without an electric field, wherein FIGS. 10A, 10C, and 10E were captured using a bright field setting and images 10B, 10D, and 10F were captured using a green fluorescent protein (GFP) filter; images 10A and 10B show dendrites before coming into contact with protein, images 10C and 10D show 15 minutes passive adsorption, and images 10E and 10F show active capture of protein after 15 minutes using a 15 Vpp, 10 kHz electric field, using a sensor element according to one embodiment; wherein the scale bar is 100 microns.

Unlike conventional SERS substrates, sensor element embodiments with electrodes as described herein may be used in an active mode in order to attract analytes to the surface using an electric field applied to the electrodes. For example, a comparison of adsorption of FITC-avidin (0.5 wt %) with and without an electric field was carried out. The SERS nanostructures used for testing were assembled on BP100 electrodes using 4/1 mM solution with an electrical signal of 3 Vpp at 10 Hz. In FIG. 10, photomicrographs A, C, and E were captured using a bright field setting and photomicrographs B, D, and F were taken using a GFP filter. In FIGS. 10A and 10B, images were taken before coming into contact with protein. In FIGS. 10C and 10D images were taken after 15 minutes of passive adsorption. In FIGS. 10E and 10F images were taken after active capture for 15 minutes using a 15 Vpp, 10 kHz electric field. The scale bar is 100 microns. Using fluorescently tagged proteins, the results (panel D vs panel F) demonstrate that an electric field substantially improves the deposition of an analyte onto the dendritic nanostructure. Similar results were obtained using GFP and a 10 Vpp, 10 kHz electric field.

SERS Enhancement Factor

The SERS enhancement factor for a sensor element with a nanostructure assembled using a 4/1 mM solution with 3 Vpp and 10 Hz electrical signal was estimated using equation (1):

$$EF = \frac{\frac{I_{SERS}}{N_{SERS}}}{\frac{I_{NR}}{N_{NR}}} \quad (1)$$

where ISERS and INR are the signal intensity on the nanostructure and on the silicon wafer, respectively. NSERS and NNR are number of analyte molecules adsorbed onto the respective surfaces. It is assumed that both NSERS and NNR are directly proportional to the concentration of R6G deposited onto the surface. An enhancement factor of $4.55 \times 10^6$ was calculated.

Galvanic Reaction

Nanostructures as described herein can also be used as a template, or they can be functionalized. As an example, a galvanic reaction using gold salts with formed silver dendrites may be used to create a bimetal nanostructure, in which the gold replaces silver atoms. The reaction must be carefully controlled to prevent destroying the underlying template during the process, such that only the outside layer of silver is replaced. Although gold produces a weaker SERS enhancement than silver, it is more biocompatible and more stable than silver and thus can be more readily used in different applications.

Figure 11:
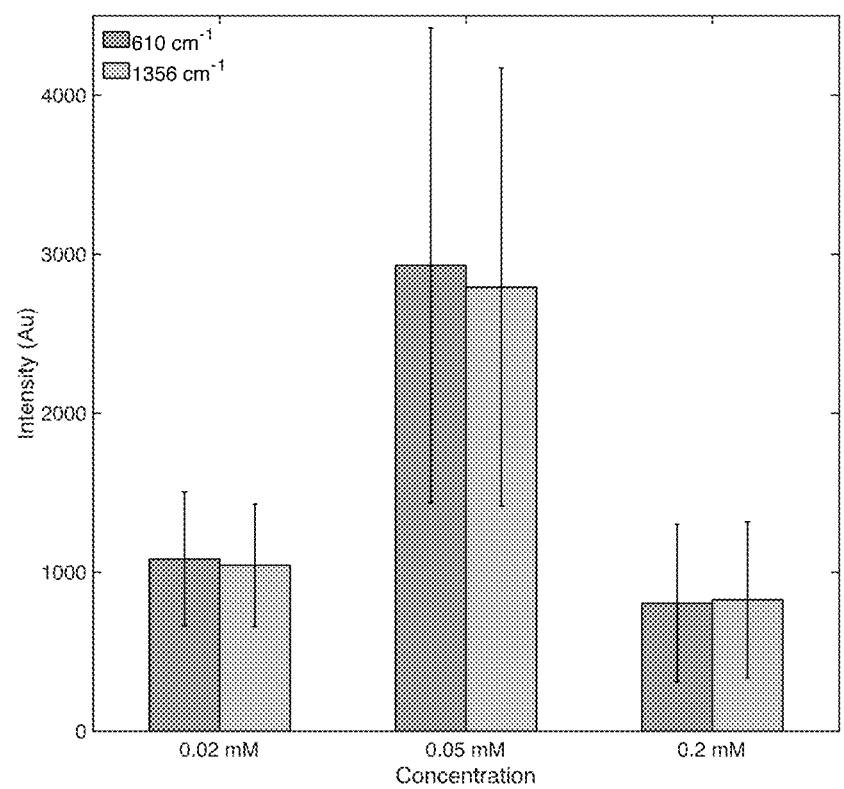
FIG. 11 is plot showing the SERS signal obtained for two R6G peaks for three different bimetallic structures.

In preliminary investigations, silver dendrites were made using a 4/1 mM solution with 3 Vpp and 10 Hz electric field applied, and then bimetallic nanostructures were prepared from these using gold salts at concentrations of 0.02 mM, 0.05 mM, and 0.2 mM gold solution. The galvanic reaction was performed by depositing a 10 μL droplet of the gold solution onto the surface of the chip for 10 minutes before washing the surface with water and air drying the sample. Visually the dendrites were a darker tone after undergoing the galvanic reaction. Energy-dispersive X-ray spectroscopy (EDS) confirmed the presence of gold in the nanostructures, and Table 1 provides the binding energy for the different elements. SERS activity of the nanostructures was tested and all three showed SERS activity. Intensity of two R6G peaks using the three bimetallic nanostructures is shown in FIG. 11.

TABLE 1

Binding energy for different elements.

| Element | $L\alpha_1$ (keV) | $L\beta_1$ (keV) |
|---------|-------------------|------------------|
| Ag      | 2.983             | 3.150            |
| Au      | 2.123             | 2.203            |
| O       | 0.525             |                  |
| Si      | 1.740             | 1.837            |

X-Ray Photoelectron Spectroscopy (XPS)

Silver nanostructures were fabricated on a silicon oxide substrate using a solution of 2 mM $Na_3C_6H_5O_7$ and 0.5 mM $AgNO_3$ and an electrical signal of 10 Hz, 3 Vpp applied for 10 minutes. XPS was performed on the nanostructures to determine their composition.

Figure 12A:
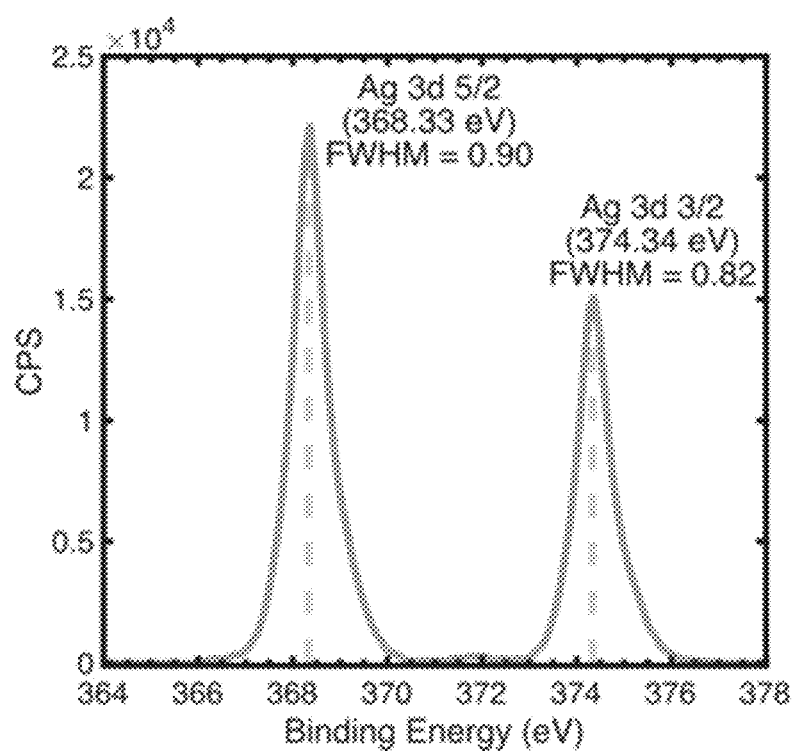
FIGS. 12A and 12B are plots showing X-ray photoelectron spectroscopy (XPS) spectra of silver nanostructures.
Figure 12B:
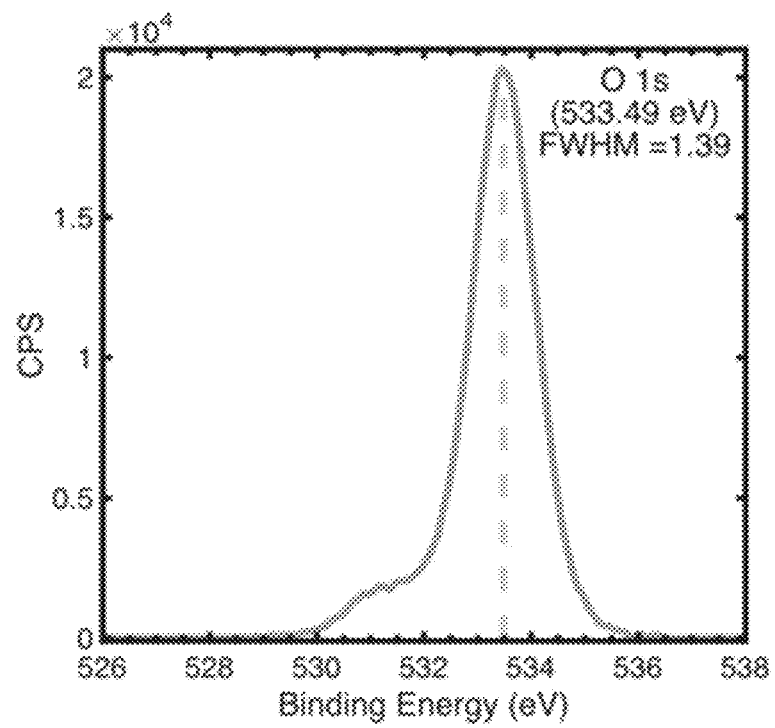

As shown in FIG. 12A, the nanostructures had single peaks for Ag 3d 5/2 and 3/2 at binding energies that match the expected values for metallic Ag with full width at half maximum (FWHM) values of 0.90 and 0.82, respectively. In FIG. 12B the O is data similarly shows little to no signal from binding energies associated with AgO or Ag2O (<530 eV), further indicating the nanostructures were composed largely if not entirely of metallic Ag. If Ag oxide was present, either the single peak would be located at a lower binding energy or a secondary peak would be present. The O is signal is attributed to the silicon oxide substrate, citrate bound to the nanostructures from formation, and water molecules still adsorbed on the surface. Thus, the data confirm that the nanostructures formed were metallic silver and not silver oxide.

All cited publications are incorporated herein by reference in their entirety.

EQUIVALENTS

While the invention has been described with respect to illustrative embodiments thereof, it will be understood that various changes may be made to the embodiments without departing from the scope of the invention. Accordingly, the described embodiments are to be considered merely exemplary and the invention is not to be limited thereby.

The invention claimed is:

1. A sensor element, comprising:
   a non-electrically conductive substrate;
   at least first and second microelectrodes, wherein at least the first microelectrode is disposed on the substrate and at least the second microelectrode is disposed in a spaced relationship from the first microelectrode;
   a metallic nanostructure substantially without metallic nanoparticles assembled along edges of at least the first microelectrode;
   wherein the non-electrically conductive substrate has a surface energy less than about 25 ergs/cm² and the metallic nanostructure is non-covalently adhered to the surface of the non-electrically conductive substrate and extends outwards from and along edges of at least the first microelectrode;
   wherein the metallic nanostructure comprises at least one stabilizing agent that promotes electrochemical growth of the metallic nanostructure from at least one metal salt without covalent bonding to the metallic nanostructure.

2. The sensor element of claim 1, wherein the nanostructure is substantially coplanar with the substrate.

3. The sensor element of claim 1, wherein the at least one metal salt comprises silver, gold, copper, platinum, aluminum, gallium, indium, rhodium, lithium, sodium, potassium, rubidium, or cesium, or a combination of one or more thereof.

4. The sensor element of claim 1, wherein the at least one stabilizing agent comprises citrate, succinate, trans-aconate, SDS, PVP, or a combination of one or more thereof.

5. The sensor element of claim 1, wherein the at least first and second microelectrodes disposed in the spaced relationship form a detection site between opposing edges of the at least first and second microelectrodes.

6. The sensor element of claim 5, wherein the metallic nanostructure is removably disposed on edges of at least the first microelectrode.

7. A sensor platform comprising the sensor element of claim 1.

8. The sensor platform of claim 7, wherein the sensor platform is selected from surface-enhanced Raman scattering (SERS), in surface plasmon resonance (SPR), localized surface plasmon resonance (LSPR), and electrical-based chemical, biochemical, and biological sensing.

9. A surface enhanced Raman spectroscopy device, comprising the sensor element of claim 1.

10. A method for analyzing a sample, comprising:
applying the sample to the metallic nanostructure of the sensor element of claim 1; and
using a technique selected from surface-enhanced Raman scattering (SERS), surface plasmon resonance (SPR), and localized surface plasmon resonance (LSPR), or an electroanalytical technique selected from coulometry, amperometry, and voltammetry, to detect an analyte in the sample.

11. The method of claim 10, wherein an electric field is present during application of the sample.

12. The method of claim 10, wherein an analyte in the sample is concentrated at the detection site.

13. The method of claim 11, wherein the sensor element comprises at least two metal microelectrodes disposed on or in close proximity to the substrate in a spaced relationship;
wherein the metallic nanostructure is formed between opposing edges of the at least two microelectrodes;
wherein the electric field is applied across the at least two electrodes.

14. A method for preparing a sensor element, comprising:
disposing at least first and second microelectrodes, wherein at least the first microelectrode is disposed on a non-electrically conductive substrate and at least the second microelectrode is disposed in a spaced relationship from the first microelectrode such that a detection site is formed between opposing edges of the at least first and second microelectrodes;
disposing a solution comprising at least one stabilizing agent and at least one metal salt on the substrate at the detection site;
wherein the substrate has a low surface energy that attracts metallic nanostructure growth by promoting interaction between the substrate and metallic nanostructure, including non-covalent adhesion and fractal and/or branched electrochemical growth of the metallic nanostructure on the low surface energy substrate outwards from and along edges of at least the first microelectrode substantially without metallic nanoparticles;
applying an AC electrical signal at a frequency of 100 Hz or lower to the at least two microelectrodes;
wherein the AC electrical signal creates an AC electric field that induces, directs, and/or influences the at least one metal salt to form the metallic nanostructure;
wherein a sensor element comprising the metallic nanostructure comprising the at least one stabilizing agent is prepared;
wherein the substrate surface energy is less than about 25 ergs/cm$^2$.

15. The method of claim 14, comprising modifying the surface of the substrate by exposing the surface to one or more agent that lowers the surface energy.

16. The method of claim 14, wherein the at least one metal salt comprises silver, gold, copper, platinum, aluminum, gallium, indium, rhodium, lithium, sodium, potassium, rubidium, or cesium, or a combination of one or more thereof.

17. The method of claim 14, wherein the at least one stabilizing agent comprises citrate, succinate, trans-aconate, SDS, PVP, or a combination of one or more thereof.

18. The method of claim 14, wherein the at least one metal salt comprises silver nitrate and the at least one stabilizing agent comprises citrate.

19. The method of claim 18, wherein a ratio of concentration of citrate to concentration of silver nitrate is from 0.5:1 to 6:1.

20. The method of claim 19, wherein a concentration of citrate is from 0.5 mM to 10 mM.

21. The method of claim 14, wherein the AC electrical signal has a frequency in the range of 0.01 Hz to 100 Hz.

22. The method of claim 14, wherein the metallic nanostructure is substantially coplanar with the substrate.

23. The method of claim 14, wherein the metallic nanostructure is removably disposed at edges of the at least first and second microelectrodes.

24. The method of claim 14, comprising removing the at least first and second microelectrodes after the metallic nanostructure is formed.

* * * * *